(12) United States Patent
Kondo (10) Patent No.: US 10,101,187 B2
(45) Date of Patent: Oct. 16, 2018

(54) FLOWMETER, DIALYSIS MACHINE AND MEDICINAL SOLUTION INJECTION DEVICE

(71) Applicant: Murata Manufacturing Co., Ltd., Kyoto (JP)

(72) Inventor: Nobuhiro Kondo, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 755 days.

(21) Appl. No.: 14/564,179

(22) Filed: Dec. 9, 2014

(65) Prior Publication Data

US 2015/0144543 A1   May 28, 2015

Related U.S. Application Data (63) Continuation of application No. PCT/JP2013/067178, filed on Jun. 24, 2013.

(30) Foreign Application Priority Data

Jul. 5, 2012  (JP) ................................ 2012-151000

(51) Int. Cl.
  B01D 35/00   (2006.01)
  G01F 1/69   (2006.01)
  (Continued)

(52) U.S. Cl.
  CPC ................. G01F 1/69 (2013.01); A61M 1/14 (2013.01); A61M 1/3663 (2013.01);
  (Continued)

(58) Field of Classification Search
  None
  See application file for complete search history.

(56) References Cited

U.S. PATENT DOCUMENTS

| 4,661,246 A | * | 4/1987 | Ash | ..................... | A61M 1/1696 |
| | | | | | 210/110 |
| 5,321,991 A | * | 6/1994 | Kalotay | ................ | G01F 1/8422 |
| | | | | | 73/861.357 |
| 2005/0240110 A1 | * | 10/2005 | Liu | ..................... | A61B 5/0031 |
| | | | | | 600/505 |

FOREIGN PATENT DOCUMENTS

| JP | 61-048722 A | 3/1986 |
| JP | H01-201263 A | 8/1989 |
| | (Continued) | |

OTHER PUBLICATIONS

International Search Report issued in Application No. PCT/JP2013/067178 dated Sep. 10, 2013.
(Continued)

*Primary Examiner* — Richard C Gurtowski
(74) *Attorney, Agent, or Firm* — Pearne and Gordon LLP (57) ABSTRACT

Provided are a flowmeter that can measure a flow rate of a liquid with high accuracy and that is easy to carry and handle, and a dialysis machine and a medicinal solution injection device that employ the flowmeter. A flowmeter includes a tube connection member and a measurement instrument body. The tube connection member includes a tube-shaped body, a plurality of resonators that are arranged with gaps there between on an inner wall surface of the body, resonator-side antennas that are connected to the plurality of resonators and a heating element that is arranged between the pluralities of resonators. The measurement instrument body includes measurement-instrument-side antennas, temperature measurement units that are connected to the measurement-instrument-side antennas and measure a temperature, and a flow rate calculation unit that calculates a flow rate on the basis of the temperatures measured by the temperature measurement units.

15 Claims, 3 Drawing Sheets

(51) Int. Cl.
*G01F 1/684* (2006.01)
*G01F 1/696* (2006.01)
*G01F 1/688* (2006.01)
*A61M 1/14* (2006.01)
*A61M 1/36* (2006.01)
*A61B 5/01* (2006.01)
*A61B 5/026* (2006.01)

(52) U.S. Cl.
CPC .............. *G01F 1/684* (2013.01); *G01F 1/688* (2013.01); *G01F 1/6882* (2013.01); *G01F 1/696* (2013.01); *A61B 5/01* (2013.01); *A61B 5/026* (2013.01); *A61M 2205/3334* (2013.01); *A61M 2205/3368* (2013.01)

(56) References Cited

FOREIGN PATENT DOCUMENTS

| JP | H02-141621 A | 5/1990 |
| JP | 2007-101450 A | 4/2007 |
| JP | 2010-266345 A | 11/2010 |

OTHER PUBLICATIONS

Written Opinion issued in Application No. PCT/JP2013/067178 dated Sep. 10, 2013.
Office Action issued in Japanese Patent Application No. 2014-523674 dated Jan. 20, 2015.

* cited by examiner

FLOWMETER, DIALYSIS MACHINE AND MEDICINAL SOLUTION INJECTION DEVICE

BACKGROUND OF THE INVENTION

Field of the Invention

The present invention relates to flowmeters that measure the flow rate of a liquid flowing inside a tube and to dialysis machines and medicinal solution injection devices that employ such a flowmeter.

Description of the Related Art

To date, various types of flowmeters that measure the flow rate of a liquid flowing inside a tube of a certain shape (hereafter, inside a tube) have been devised. Such a flowmeter is, for example, provided in a dialysis machine described in Patent Document 1 and is used in a case where, for example, the flow rate of blood is measured and control is performed so that the blood flows at a constant flow rate.

In Patent Document 2, a thermal-type flowmeter is described as an example of such a flowmeter that measures the flow rate of a liquid flowing inside a tube. In the flowmeter described in Patent Document 2, a plurality of thermally sensitive resistance wires are wound around an outer wall surface of a tube through which a liquid flows, the liquid being a target of flow rate measurement. The plurality of thermally sensitive resistance wires is wound at different positions from one another in the direction in which the liquid flows (upstream side and downstream side). A heater is mounted on the outer wall surface of the tube between the position at which the thermally sensitive resistance wire is arranged on the upstream side and the position at which the thermally sensitive resistance wire is arranged on the downstream side.

In the flowmeter described in Patent Document 2, the liquid inside the tube is heated by the heater. In the case where the liquid inside the tube is not flowing, the temperature sensed by the thermally sensitive resistance wire on the upstream side and temperature sensed by the thermally sensitive resistance wire on the downstream side are the same. In the case where the liquid is flowing inside the tube, the liquid heated by the heater flows toward the downstream side and therefore the temperature sensed by the thermally sensitive resistance wire on the downstream side is higher than the temperature sensed by the thermally sensitive resistance wire on the upstream side. Since the difference between the temperature sensed by the thermally sensitive resistance wire on the upstream side and the temperature sensed by the thermally sensitive resistance wire on the downstream side at this time is dependent upon the flow rate of the liquid flowing inside the tube, the flow rate is calculated in the flowmeter described in Patent Document 2 by detecting this difference in temperature.

Patent Document 1: Japanese Unexamined Patent Application Publication No. 1-201263

Patent Document 2: Japanese Unexamined Patent Application Publication No. 2-141621

BRIEF SUMMARY OF THE INVENTION

In the flowmeter described in Patent Document 2, the temperature of a liquid flowing inside a tube is sensed by thermally sensitive resistance wires arranged around the outside of the tube. Consequently, the heat of the liquid transmitted to the outside via the wall of the tube is sensed by the thermally sensitive resistance wire rather than the temperature of the liquid and as a result, the temperature of the liquid cannot be measured with high accuracy. In addition, it is necessary to have a measurement instrument body, which is equipped with a temperature measurement unit that measures the temperature sensed by the thermally sensitive resistance wires and a flow rate calculation unit that calculates a flow rate of the liquid flowing inside the tube by using the temperature output by the temperature measurement unit, attached to the tube at all times. Consequently, the flowmeter is large in size as a whole, and carrying and handling the flowmeter is not easy.

Therefore, an object of the present invention is to provide a flowmeter that is capable of measuring the flow rate of a liquid flowing inside a tube with high accuracy, that has a detachable measurement instrument body equipped with a flow rate calculation unit, and that can be easily carried and handled, and to provide a dialysis machine and a medicinal solution injection device that employ the flowmeter.

The present invention relates to a flowmeter that measures a flow rate of a liquid flowing inside a tube and has the following characteristics. The flowmeter includes a tube connection member and a measurement instrument body.

The tube connection member includes a body that is tube shaped, a plurality of resonators arranged with gaps therebetween on an inner wall surface of the body, a resonator-side antenna that is connected to the plurality of resonators, and a heating element that is arranged between the pluralities of resonators.

The measurement instrument body includes a measurement-instrument-side antenna, a temperature measurement unit that is connected to the measurement-instrument-side antenna and measures a temperature, and a flow rate calculation unit that calculates a flow rate on the basis of a temperature measured by the temperature measurement unit.

With this configuration, resonance signals generated in the resonators arranged in the tube connection member are wirelessly transmitted to the measurement instrument body. Thus, the flow rate can be measured in a state where only the tube connection member is connected to the tube and carrying and handling of the flowmeter is easy. In addition, since the resonators are arranged on the inner wall surface of the tube-shaped body, resonance signals having resonant frequencies that correspond to the temperature of the liquid with high accuracy are obtained and the temperature and the flow rate can be measured with high accuracy.

In addition, in the flowmeter of the present invention, it is preferable that the heating element be an element that is supplied with electricity by electromagnetic field coupling and is embedded in the tube connection member. With this configuration, the circuit that drives the heating element can be formed so as to be separate from the tube connection member, and therefore it is easier to carry and handle the flowmeter. In addition, since the heating element can be arranged at a position closer to the liquid, the amount of heat that is internally transmitted to the wall surface of the tube connection member is reduced. Therefore, the liquid can be effectively heated and transmission of heat to the resonators via the wall of the tube connection member can be suppressed.

In addition, in the flowmeter of the present invention, it is preferable that the heating element be arranged outside of the tube connection member and close to the tube connection member. In this case, the number of components of the tube connection member can be reduced.

In addition, in the flowmeter of the present invention, it is preferable that the tube connection member includes a rectifying member arranged inside the tube connection member. With this configuration, a liquid flow in which the liquid flows from one resonator to the heating element and then to the other resonator can be more accurately realized. Thus, the measurement accuracy of the flow rate is improved.

In addition, the present invention relates to a dialysis machine, the dialysis machine including the flowmeter having any of the above-described characteristics, and a tube that is connected to the flowmeter, the dialysis machine controlling a flow rate of blood flowing in the tube in accordance with the flow rate calculated by the flow rate calculation unit. In addition, the present invention relates to a medicine injection device, the medicine injection device including the flowmeter having any of the above-described characteristics and a tube connected to the flowmeter.

With this configuration, the flow rate can be measured with high accuracy and therefore the flow rate can be controlled with high accuracy.

According to the present invention, a flowmeter can be realized that is capable of measuring the flow rate of a liquid flowing inside a tube with high accuracy, that includes a detachable measurement instrument body equipped with a flow rate calculation unit, and that is easy to carry and handle.

DETAILED DESCRIPTION OF THE INVENTION

Figure 1:
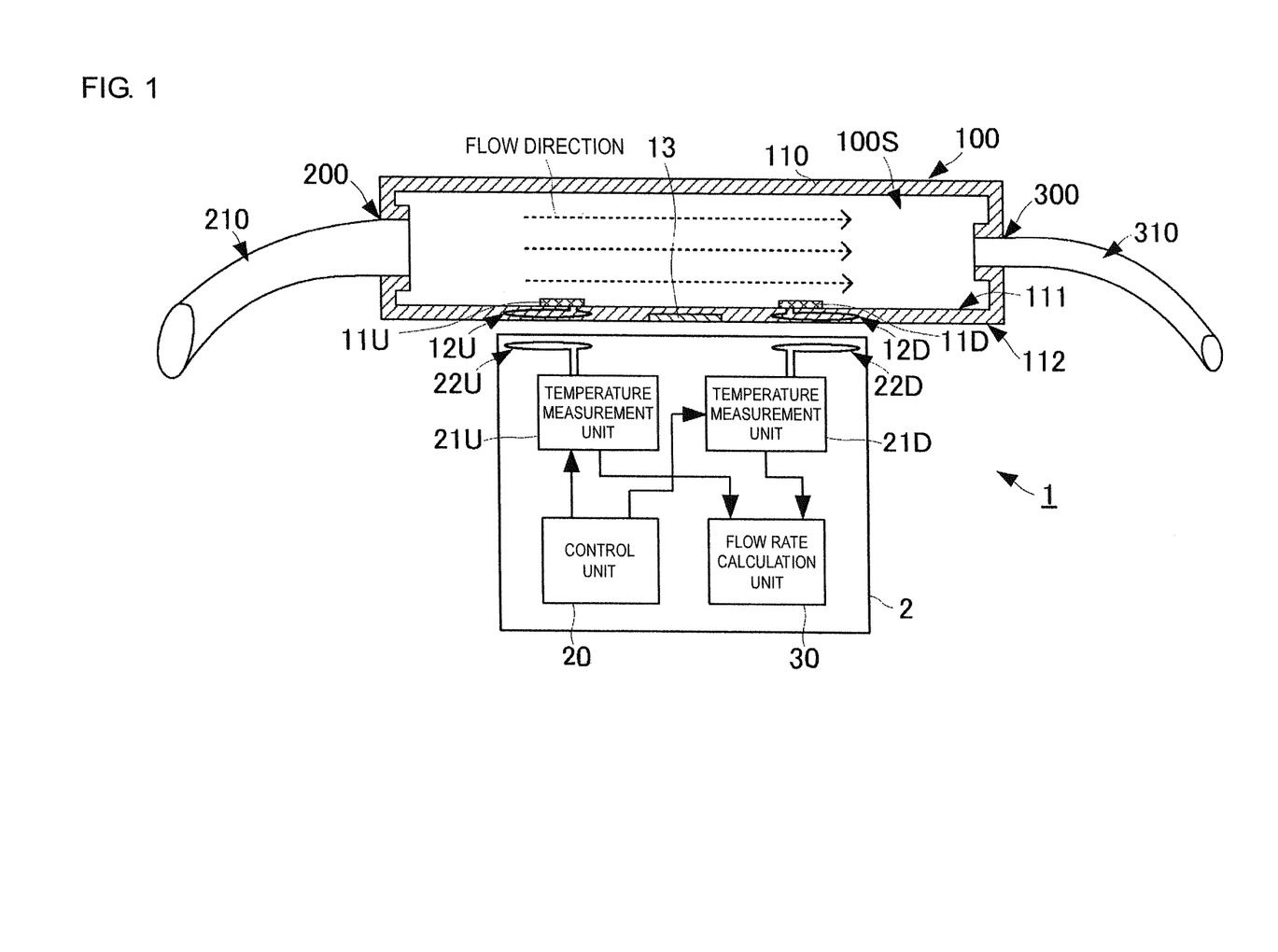
FIG. 1 is a structural diagram illustrating the configuration of a flowmeter according to a first embodiment of the present invention.

A flowmeter according to a first embodiment of the present invention will be described while referring to the drawings. FIG. 1 is a structural diagram illustrating the configuration of a flowmeter 1 according to the first embodiment of the present invention.

The flowmeter 1 includes a tube connection member 100 and a measurement instrument body 2. The tube connection member 100 and the measurement instrument body 2 are separate bodies.

The tube connection member 100 includes a tube-shaped body 110. The body 110 includes an outer peripheral wall that extends in the longitudinal direction and end walls that are arranged on either side in the longitudinal direction. A tube internal space 100S is formed by the outer peripheral wall and the end walls. The outer peripheral wall and the end walls are formed so as to be integrated with each other and are composed of an insulating material such as a resin. A tube connection hole 200 is formed in an end wall of the body 110 on one side in the longitudinal direction. A tube connection hole 300 is formed in an end wall of the body 110 on the other side in the longitudinal direction. One end of a tube 210 is inserted into the tube connection hole 200 and the tube 210 is connected to the tube connection member 100. One end of a tube 310 is inserted into the tube connection hole 300 and the tube 310 is connected to the tube connection member 100. The direction in which the tubes 210 and 310 extend is the same as a direction in which the liquid flows and is the same as the longitudinal direction of the body 110.

With this configuration, a liquid (for example blood) flows into the inside of the tube internal space 100S of the tube connection member 100 via the tube 210. The liquid flows through the inside of the tube internal space 100S in the longitudinal direction of the body 110 and flows out into the tube 310. At this time, the liquid is controlled so as to flow at such a flow rate that at least the tube internal space 100S is filled.

The tube connection member 100 is equipped with a resonator 11U and a resonator 11D. The resonators 11U and 11D are arranged on an inner wall surface 111 of the outer peripheral wall of the body 110, that is, on a surface of the outer peripheral wall of the body 110 on the tube internal space 100S side. The resonators 11U and 11D are arranged with a certain gap therebetween in the longitudinal direction of the body 110.

The resonators 11U and 11D are elements whose resonant frequencies change with temperature. For example, the resonators 11U and 11D are crystal resonators.

The tube connection member 100 is equipped with a resonator-side antenna 12U and a resonator-side antenna 12D. The resonator-side antennas 12U and 12D are arranged inside the outer peripheral wall of the body 110. The resonator-side antennas 12U and 12D are composed of loop-shaped conductors. The two ends of the loop-shaped conductor of the resonator-side antenna 12U are connected to the resonator 11U. The two ends of the loop-shaped conductor of the resonator-side antenna 12D are connected to the resonator 11D. With this configuration, a resonance signal generated by the resonator 11U is transmitted (radiated) from the resonator-side antenna 12U to the outside. In addition, a resonance signal generated by the resonator 11D is transmitted (radiated) from the resonator-side antenna 12D to the outside. A temperature sensor is formed of the resonator 11U and the resonator-side antenna 12U. In addition, a temperature sensor is formed of the resonator 11D and the resonator-side antenna 12D.

Figure 2:
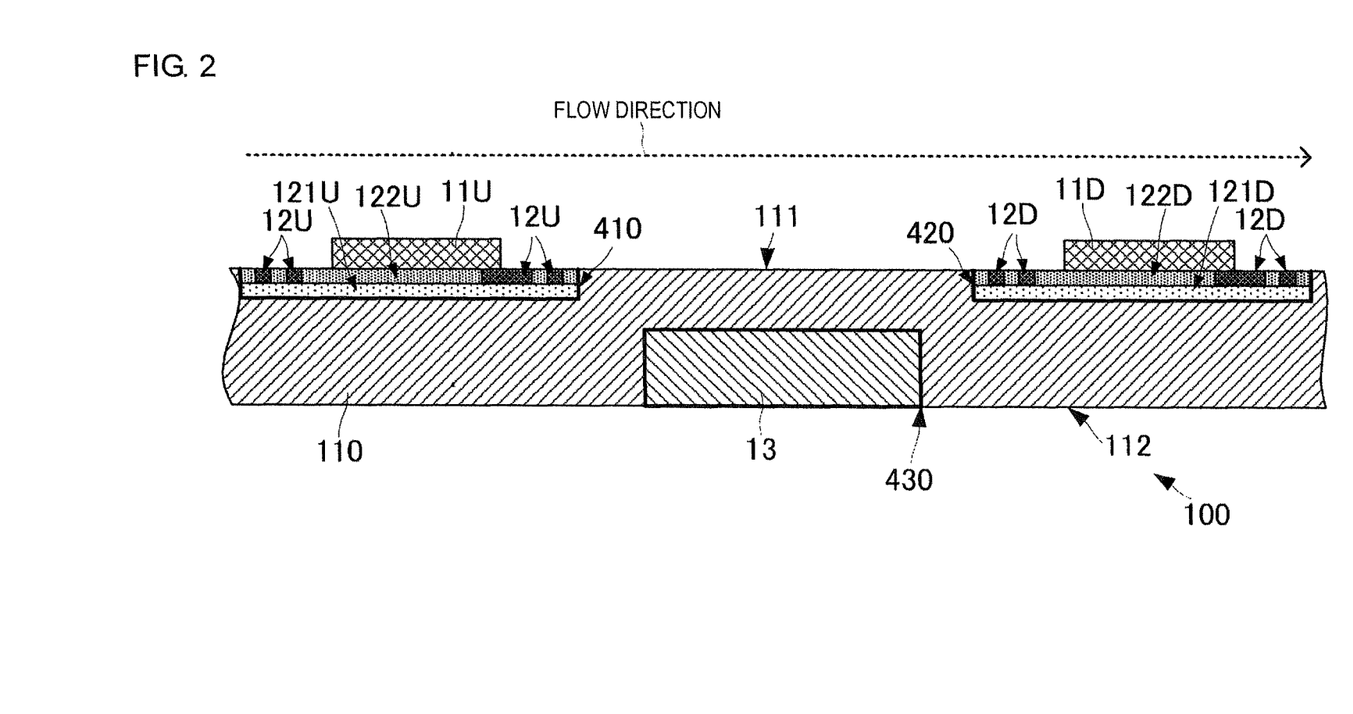
FIG. 2 is a partial, enlarged view of the body of a tube connection member that is included in the flowmeter according to the first embodiment of the present invention.

FIG. 2 is a partial enlarged view of the body 110 of the tube connection member 100 that is included in the flowmeter 1 according to the first embodiment of the present invention. The resonators 11U and 11D and the resonator-side antennas 12U and 12D are arranged in the body 110 as illustrated in FIG. 2.

A concavity 410 is provided in the inner wall surface 111 of the outer peripheral wall of the body 110 of the tube connection member 100. A base sheet 121U is arranged on the bottom surface of the concavity 410. The resonator-side antenna 12U and an insulating layer 122U are provided on one main surface of the base sheet 121U.

The resonator 11U is arranged on a surface of the insulating layer 122U on the tube internal space 100S side. Consequently, the resonator 11U is not in contact with the outer peripheral wall of the body 110 of the tube connection member 100. The resonator 11U is connected to the two ends of the resonator-side antenna 12U on the surface of the insulating layer 122U.

A concavity 420 is provided in the inner wall surface 111 of the outer peripheral wall of the body 110 of the tube connection member 100. A base sheet 121D is arranged on the bottom surface of the concavity 420. The resonator-side antenna 12D and an insulating layer 122D are provided on one main surface of the base sheet 121D.

The resonator 11D is arranged on a surface of the insulating layer 122D on the tube internal space 100S side.

Consequently, the resonator 11D is not in contact with the outer peripheral wall of the body 110 of the tube connection member 100. The resonator 11D is connected to the two ends of the resonator-side antenna 12D on the surface of the insulating layer 122D.

A concavity 430 is provided in an outer wall surface 112 of the outer peripheral wall of the body 110 of the tube connection member 100. A heating element 13 is arranged in the concavity 430. The heating element 13 is composed of for example an electrically heated wire that generates heat when supplied with a current from a power supply, which is not illustrated. The heating element 13 is arranged between the resonator 11U and the resonator 11D in the longitudinal direction of the body 110 of the tube connection member 100.

The measurement instrument body 2 includes a casing. The measurement instrument body 2 includes a control unit 20, temperature measurement units 21U and 21D, measurement-instrument-side antennas 22U and 22D, and a flow rate calculation unit 30, and these components are arranged inside the casing.

The control unit 20 is connected to the temperature measurement units 21U and 21D. The temperature measurement unit 21U is connected to the measurement-instrument-side antenna 22U. The temperature measurement unit 21D is connected to the measurement-instrument-side antenna 22D. The temperature measurement units 21U and 21D are connected to the flow rate calculation unit 30.

As well as performing overall control of the measurement instrument body 2, the control unit 20 performs control to cause the temperature measurement units 21U and 21D to generate an excitation signal when a flow rate measurement operation input is performed from an operation unit, which is not illustrated.

The temperature measurement unit 21U generates a first excitation signal and outputs the first excitation signal to the measurement-instrument-side antenna 22U. The first excitation signal is a signal including a frequency band component that includes a range of resonant frequencies that can be obtained by the resonator 11U in the measurement temperature range.

The measurement-instrument-side antenna 22U is formed so as to be able to radiate the first excitation signal. In addition, the measurement-instrument-side antenna 22U is formed so as to be able receive a first resonance signal generated by the resonator 11U and transmitted from the resonator-side antenna 12U.

The temperature measurement unit 21D generates a second excitation signal and outputs the second excitation signal to the measurement-instrument-side antenna 22D. The second excitation signal is a signal including a frequency band component that includes a range of resonant frequencies that can be obtained by the resonator 11D in the measurement temperature range.

The measurement-instrument-side antenna 22D is formed so as to be able to radiate the second excitation signal. In addition, the measurement-instrument-side antenna 22D is formed so as to be able receive a second resonance signal generated by the resonator 11D and transmitted from the resonator-side antenna 12D.

The temperature measurement unit 21U detects a frequency of the received first resonance signal (resonance signal generated by the resonator 11U) and calculates a first temperature from the detected frequency. Thus, the temperature measurement unit 21U is able to measure a first temperature sensed by the resonator 11U.

The temperature measurement unit 21D detects a frequency of the received second resonance signal (resonance signal generated by the resonator 11D) and calculates a second temperature from the detected frequency. Thus, the temperature measurement unit 21D is able to measure a second temperature sensed by the resonator 11D.

The flow rate calculation unit 30 calculates the flow rate of the liquid from the first temperature and the second temperature. The flow rate can be calculated by using the concept outlined below.

When the heating element 13 is supplied with a current from a power supply, which is not illustrated, so as to be made to generate heat, the liquid inside the tube internal space 100S is heated via the outer wall surface 112 of the outer peripheral wall of the body 110 of the tube connection member 100. Here, if the liquid is not flowing inside the tube internal space 100S, the temperature of the liquid has a temperature distribution in which the temperature is highest at positions in the vicinity of the heating element 13 and decreases the closer one comes to the end walls of the body 110. Consequently, if the distance between the heating element 13 and the resonator 11U is the same as the distance between the heating element 13 and the resonator 11D in the longitudinal direction of the body 110, the temperature of the liquid sensed by the resonator 11U and the temperature of the liquid sensed by the resonator 11D are the same. On the other hand, if the liquid is flowing inside the tube internal space 100S, the liquid inside the tube internal space 100S that has been heated by the heating element 13 flows in a downstream direction. For example, with the above-described example configuration, since the liquid flows from the resonator 11U side toward the resonator 11D side via the position of the heating element 13 in the longitudinal direction of the body 110, the liquid heated by the heating element 13 flows toward the resonator 11D side. Consequently, the temperature of the liquid has a temperature distribution in which the temperature is lowest at positions in the vicinity of the resonator 11U, is highest at positions in the vicinity of the heating element 13, and decreases as one approaches the end wall of the body 110 on the resonator 11D side from the heating element 13. Therefore, the temperature of the liquid sensed by the resonator 11D is higher than the temperature of the liquid sensed by the resonator 11U and this temperature difference is dependent on the speed at which the liquid flows, in other words, the flow rate.

Using this principle, the flow rate calculation unit 30 calculates the difference between the first temperature and the second temperature. The flow rate calculation unit 30 stores in advance an expression that expresses the relationship between the difference and the flow rate, and calculates the flow rate from the calculated difference. Alternatively, the flow rate calculation unit 30 stores in advance a table that expresses the relationship between the difference and the flow rate, and reads out the flow rate associated with the calculated difference in order to calculate the flow rate.

The flowmeter 1 having the above-described configuration operates as follows.

The control unit 20 of the measurement instrument body 2 controls the generation of the excitation signals by the temperature measurement units 21U and 21D on the basis of on operation input made on the flowmeter side from an operation unit, which is not illustrated. The temperature measurement unit 21U generates the first excitation signal in accordance with the control of the generation of excitation signals and outputs the first excitation signal to the measurement-instrument-side antenna 22U. The measurement-instrument-side antenna 22U radiates the first excitation signal. The temperature measurement unit 21D generates the second excitation signal in accordance with the control of the generation of excitation signals and outputs the second excitation signal to the measurement-instrument-side antenna 22D. The measurement-instrument-side antenna 22D radiates the second excitation signal. The radiation timing of the first excitation signal and the radiation timing of the second excitation signal are controlled so as to be substantially the same.

Simultaneously with the control of the generation of excitation signals or before the generation of the excitation signals, the heating element 13 is subjected to heating control in accordance with control performed by the control unit 20 and the heating element 13 is supplied with a current from a power supply, which is not illustrated, and as a result generates heat at a certain temperature. Thus, the liquid is heated so as to reach a certain temperature.

The resonator-side antenna 12U receives the first excitation signal and then outputs the first excitation signal to the resonator 11U. The resonator 11U is excited by the first excitation signal, resonates at a resonant frequency corresponding to the temperature of the liquid at the position of the resonator 11U and is caused to generate a first resonance signal. The first resonance signal is output to the resonator-side antenna 12U and the resonator-side antenna 12U radiates the first resonance signal.

The resonator-side antenna 12D receives the second excitation signal and then outputs the second excitation signal to the resonator 11D. The resonator 11D is excited by the second excitation signal, resonates at a resonant frequency corresponding to the temperature of the liquid at the position of the resonator 11D, and generates a second resonance signal. The second resonance signal is output to the resonator-side antenna 12D and the resonator-side antenna 12D radiates the second resonance signal.

The measurement-instrument-side antenna 22U receives the first resonance signal and outputs the first resonance signal to the temperature measurement unit 21U. The temperature measurement unit 21U measures the first temperature from the first resonance signal. The measurement-instrument-side antenna 22D receives the second resonance signal and outputs the second resonance signal to the temperature measurement unit 21D. The temperature measurement unit 21D measures the second temperature from the second resonance signal.

The flow rate calculation unit 30 calculates the flow rate from the difference (temperature difference) between the first temperature and the second temperature.

With the above-described configuration, temperature information can be transmitted using radio signals and therefore the flow rate of the liquid can be measured without mounting the measurement instrument body on the tube through which the liquid flows. In other words, along with the tube-shaped tube connection member 100, only the resonators 11U and 11D, the resonator-side antennas 12U and 12D and the heating element 13 are connected to the tubes 210 and 310. Thus, the flowmeter 1 that is easy to carry and handle can be realized.

In addition, since the resonators 11U and 11D, which sense the temperature of the liquid, are arranged in the tube internal space 100S, the temperature of the liquid can be sensed with high accuracy and the temperature of the liquid can be measured with high accuracy. Thus, the flow rate can be calculated with high accuracy.

In addition, when the configuration of this embodiment is used, the measurement instrument body 2, which is made up of comparatively expensive components, can be made as a separate body to the tube connection member 100, which is made up of comparatively inexpensive components, and therefore the tube connection member 100 can be used as a disposable component. Thus, in the case where the flowmeter 1 is to be used in control of the flow rate in a dialysis machine for example, just the tube connection member 100 through which blood flows can be disposed of after being used and the measurement instrument body 2 can be repeatedly used. Therefore, the flowmeter 1 that is hygienic and for which cost is comparatively not a concern can be realized. In addition, since it is possible to structure the tube connection member 100 so that it does not need to be electrically connected to the outside, malfunctions such as corrosion of exposed electrodes or contact defects caused by corrosion of electrodes do not occur even when the tube connection member 100 is exposed in an environment in which it is wet with water or washed for example.

Figure 3:
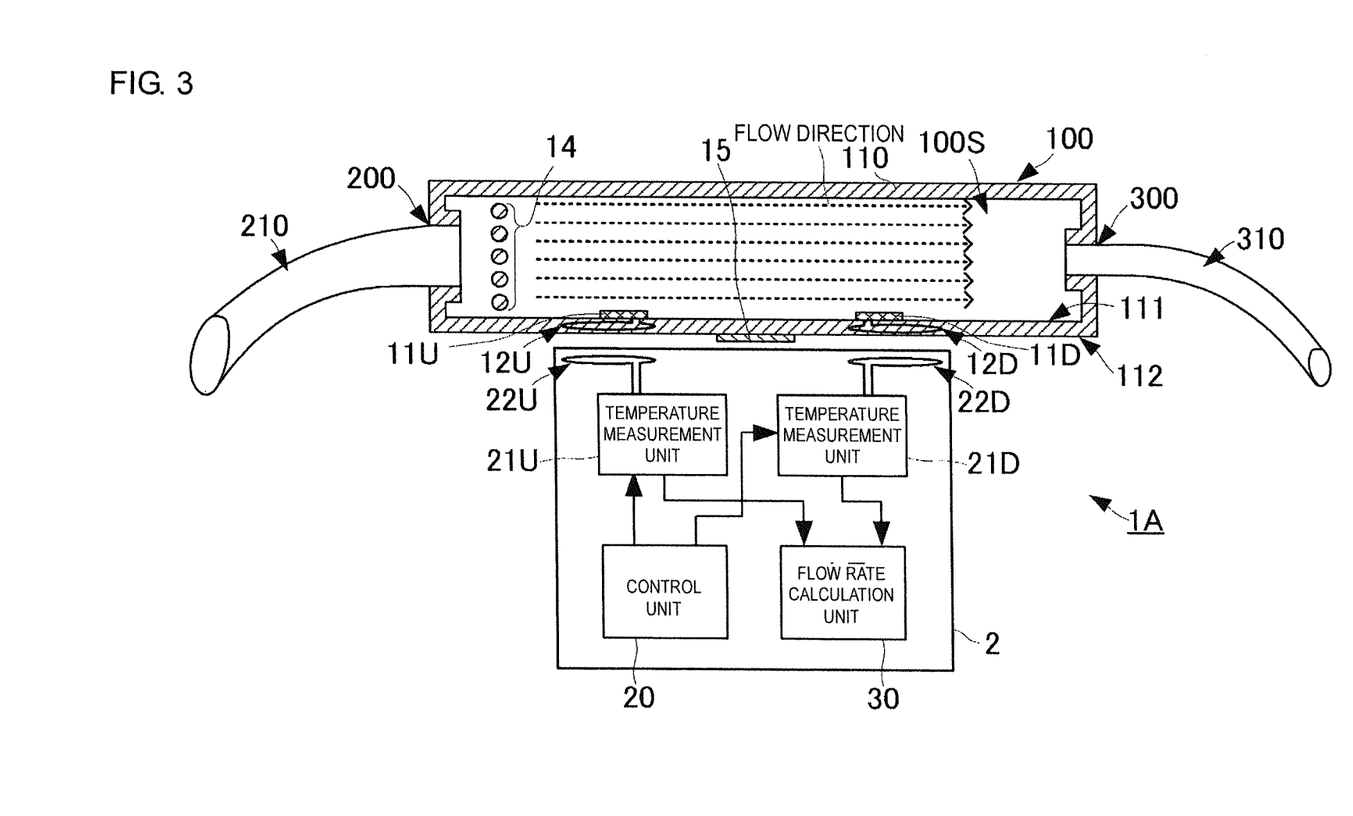
FIG. 3 is a structural diagram illustrating the configuration of a flowmeter according to a second embodiment of the present invention.

Next, a flowmeter according to a second embodiment will be described while referring to the drawings. FIG. 3 is a structural diagram illustrating the configuration of a flowmeter according to the second embodiment of the present invention. A flowmeter 1A of this embodiment differs from the flowmeter 1 according to the first embodiment in that it is further equipped with a rectifying (flow straightening) element 14 that is arranged inside the tube internal space 100S of the tube connection member 100 and in that it is equipped with a heating element 15 instead of the heating element 13. The heating element 15 is arranged separately outside of the tube connection member 100 and close to the tube connection member 100. The rest of the configuration of the flowmeter 1A of this embodiment is the same as that of the flowmeter 1 according to the first embodiment. Therefore, only points that are different to the flowmeter 1 according to the first embodiment will be described.

The rectifying element 14 is arranged between the tube connection hole 200 and the resonator 11U in the longitudinal direction of the body 110 inside the tube internal space 100S of the body 110 of the tube connection member 100. The rectifying element 14 performs rectification such that the liquid that flows in from the tube connection hole 200 flows straight in the longitudinal direction of the body 110.

As a result of providing the rectifying element 14, the liquid flows smoothly and correctly in the order of the position of the resonator 11U, the position of the heating element 15 and the position of the resonator 11D. Therefore, the flow rate of the liquid can be measured with higher accuracy. The heating element 15 heats the liquid similarly to the heating element 13. By using the heating element 15 instead of the heating element 13, the number of components of the tube connection member 100 can be reduced.

The flowmeter 1A having the above-described configuration is used in a dialysis machine for example. When the flowmeter 1A is used in a dialysis machine, the above-mentioned liquid is blood. The flow rate of blood needs to be controlled in a dialysis machine. Here, the flow rate of blood can be measured with high accuracy and the flow rate of blood can be controlled with high accuracy by using the flowmeter 1A having the above-described configuration. In addition, it is possible to easily replace just the tube connection member 100 after the tube connection member 100 has been contaminated with blood. In addition, the flowmeter 1A having the above-described configuration can be used as a flow rate sensor or a blockage sensor of a medicinal solution injection machine.

In the above-described embodiment, a structure has been described in which the resonators 11U and 11D protrude from the inner wall surface 111 into the tube internal space 100S, but the surfaces of the resonators 11U and 11D may instead be arranged so as to coincide with the inner wall surface 111. If this configuration is adopted, the flow of the liquid will not be affected by the resonators 11U and 11D. Thus, the flow of the liquid can be made smoother.

In addition, in the above-described embodiments, examples have been described in which the heating elements 13 and 15 are arranged on the outer wall surface 112 of the outer peripheral wall of the body 110 of the tube connection member 100. However, if a heating element is used to which electricity is supplied by electromagnetic field coupling, the heating element can be embedded inside the outer peripheral wall of the body 110 of the tube connection member 100. Thus, the heating element can be moved closer to the tube internal space 100S of the body 110 and the liquid can be heated more efficiently. In addition, since the liquid is efficiently heated, the amount of heat generated by the heating element in order to heat the liquid to the certain temperature can be reduced and the amount of heat generated by the heating element that is transmitted to the resonators via the outer peripheral wall can be suppressed. Thus, the resonators can more accurately sense the temperature of the liquid.

In addition, in the above-described embodiments, examples were described in which the temperature measurement units 21U and 21D and the measurement-instrument-side antennas 22U and 22D are individually provided for the resonators 11U and 11D, but a common temperature measurement unit and a common measurement-instrument-side antenna may instead be provided. In such a case, a single temperature measurement unit generates an excitation signal that has a frequency band including the resonant frequencies of the resonators 11U and 11D and a single measurement-instrument-side antenna transmits the excitation signal. Thus, the structures of the temperature measurement unit and the measurement instrument body can be simplified.

In addition, in the above-described embodiments, a heat insulating material may be arranged between the heating elements 13 and 15, the resonators 11U and 11D and the resonator-side antennas 12U and 12D. Thus, transmission of heat generated by the heating elements 13 and 15 to the resonators 11U and 11D and the resonator-side antenna 12U and 12D via the body 110 of the tube connection member 100 can be suppressed and the temperature can be measured with higher accuracy. Therefore, the flow rate can be calculated with higher accuracy.

In addition, in the above-described embodiments, examples have been described in which the resonators 11U and 11D are directly in contact with the liquid, but a protective film having high thermal conductivity and high liquid resistance to the liquid that is to be measured may be provided on the inner wall surface 111 of the body 110 of the tube connection member 100 containing the resonators 11U and 11D.

In addition, in the above-described embodiments, examples have been described in which the resonator-side antennas 12U and 12D are arranged inside the body 110 of the tube connection member 100, but instead a conductor pattern on the radiating surfaces of the resonator-side antennas 12U and 12D may be exposed through the outer wall surface 112 of the body 110. Thus, the propagation distance of the measurement-instrument-side antennas 22U and 22D can be extended.

REFERENCE SIGNS LIST 1, 1A: flowmeter,
2: measurement instrument body,
11U, 11D: resonator,
12U, 12D: resonator-side antenna,
13, 15: heating element,
14: rectifying element,
20: control unit,
21U, 21D: temperature measurement unit,
22U, 22D: measurement-instrument-side antenna,
30: flow rate calculation unit,
100: tube connection member,
110: body,
111: inner wall surface,
112: outer wall surface,
121U, 121D: base sheet,
122U, 122D: insulating layer,
200, 300: tube connection hole,
210, 310: tube,
410, 420, 430: concavity,

The invention claimed is:

1. A flowmeter comprising:
a tube connection member; and
a measurement instrument body;
wherein the tube connection member includes:
a body that is tube shaped,
a plurality of resonators arranged with gaps therebetween on an inner wall surface of the body,
a resonator-side antenna that is connected to the plurality of resonators, and
a heating element that is arranged between the plurality of resonators, and
wherein the measurement instrument body includes:
a measurement-instrument-side antenna,
a temperature measurement unit that is connected to the measurement-instrument-side antenna and measures a temperature of the plurality of resonators, and
a flow rate calculation unit that calculates a flow rate on the basis of the temperature of the plurality of resonators measured by the temperature measurement unit.

2. The flowmeter according to claim 1, wherein the heating element is an element that is supplied with electricity by electromagnetic field coupling and is embedded in the tube connection member.

3. The flowmeter according to claim 1, wherein the heating element is arranged outside of the tube connection member and adjacent to the tube connection member.

4. The flowmeter according to claim 1, wherein the tube connection member includes a flow straightening member arranged inside the tube connection member.

5. A dialysis machine comprising:
the flowmeter according to claim 1 and a tube that is connected to the flowmeter,
the dialysis machine controlling a flow rate of blood flowing in the tube in accordance with the flow rate calculated by the flow rate calculation unit.

6. A medicine injection device comprising:
the flowmeter according to claim 1; and a tube connected to the flowmeter.

7. The flowmeter according to claim 2, wherein the tube connection member includes a flow straightening member arranged inside the tube connection member.

8. The flowmeter according to claim 3, wherein the tube connection member includes a flow straightening member arranged inside the tube connection member.

9. A dialysis machine comprising:
the flowmeter according to claim 2 and a tube that is connected to the flowmeter, the dialysis machine controlling a flow rate of blood flowing in the tube in accordance with the flow rate calculated by the flow rate calculation unit.

10. A dialysis machine comprising:
the flowmeter according to claim 3 and a tube that is connected to the flowmeter,
the dialysis machine controlling a flow rate of blood flowing in the tube in accordance with the flow rate calculated by the flow rate calculation unit.

11. A dialysis machine comprising:
the flowmeter according to claim 4 and a tube that is connected to the flowmeter,
the dialysis machine controlling a flow rate of blood flowing in the tube in accordance with the flow rate calculated by the flow rate calculation unit.

12. A medicine injection device comprising:
the flowmeter according to claim 2; and a tube connected to the flowmeter.

13. A medicine injection device comprising:
the flowmeter according to claim 3; and a tube connected to the flowmeter.

14. A medicine injection device comprising:
the flowmeter according to claim 4; and a tube connected to the flowmeter.

15. The flowmeter comprising according to claim 1, wherein the resonator-side antenna that is connected to the plurality of resonators is arranged within the outer peripheral wall of the body.

* * * * *

UNITED STATES PATENT AND TRADEMARK OFFICE
CERTIFICATE OF CORRECTION

PATENT NO. : 10,101,187 B2  
APPLICATION NO. : 14/564179  
DATED : October 16, 2018  
INVENTOR(S) : Nobuhiro Kondo

Page 1 of 1

It is certified that error appears in the above-identified patent and that said Letters Patent is hereby corrected as shown below:

In the Claims

Claim 15, Column 11, Line 27: "within the outer peripheral" should read --within an outer peripheral--

Signed and Sealed this
Twenty-first Day of May, 2019

Andrei Iancu
*Director of the United States Patent and Trademark Office*